United States Patent [19]

Pankow

[11] Patent Number: 5,439,572
[45] Date of Patent: Aug. 8, 1995

[54] LENS PROTECTIVE ENCASEMENT PACKET

[75] Inventor: Mark L. Pankow, Chicago, Ill.

[73] Assignee: Isoclear, Inc., Chicago, Ill.

[21] Appl. No.: 90,300

[22] Filed: Jul. 12, 1993

Related U.S. Application Data

[63] Continuation-in-part of Ser. No. 800,686, Dec. 12, 1991, Pat. No. 5,227,039.

[51] Int. Cl.⁶ .............................. G02C 13/00
[52] U.S. Cl. ...................... 204/180.1; 204/299 R; 134/901; 206/5.1
[58] Field of Search .............. 204/299 R, 180.1; 134/901; 206/5.1

[56] References Cited

U.S. PATENT DOCUMENTS

| | | | |
|---|---|---|---|
| Re. 32,672 | 5/1988 | Huth et al. | 252/95 |
| 2,843,540 | 7/1958 | Ressler | 204/180 |
| 2,932,383 | 4/1960 | Fagan | 206/5.1 X |
| 2,967,607 | 1/1961 | Hollinger | 206/5.1 X |
| 3,037,616 | 6/1962 | Phipps, III | 206/5.1 X |
| 3,054,412 | 9/1962 | Nickell | 134/137 |
| 3,056,998 | 10/1962 | Ebner | 134/901 X |
| 3,083,819 | 4/1963 | Entzminger | 134/901 X |
| 3,089,500 | 5/1963 | Stalcup | 134/156 |
| 3,149,364 | 9/1964 | Baptist et al. | 15/506 |
| 3,317,417 | 5/1967 | Raymond | 204/299 |
| 3,344,461 | 10/1967 | Floor | 206/5.1 X |
| 3,369,656 | 2/1968 | Skinner, Jr. | 206/5.1 X |
| 3,494,846 | 2/1970 | Arquembourg | 204/180 |
| 3,725,226 | 3/1973 | Stoner | 204/149 |
| 3,764,513 | 10/1973 | Saravis | 204/299 |
| 3,808,118 | 8/1974 | Golias | 204/299 |
| 3,871,395 | 3/1975 | Murry | 134/107 |
| 3,896,021 | 7/1975 | Fosslien | 204/299 |
| 3,908,680 | 9/1975 | Krezanoski | 134/27 |
| 3,930,973 | 7/1976 | Nerenberg | 2304/180 |
| 3,962,069 | 6/1976 | Inoue et al. | 204/300 |
| 3,977,517 | 8/1976 | Kadlecik et al. | 206/5.1 |
| 3,990,579 | 11/1976 | Manning | 206/501 |
| 4,096,870 | 6/1978 | Manfuso, Jr. | 134/28 |
| 4,187,574 | 2/1980 | Wrue | 15/104.92 |
| 4,202,740 | 5/1980 | Stoner et al. | 204/130 |
| 4,223,782 | 9/1980 | Giambalvo | 106/3.1 |
| 4,263,054 | 4/1981 | Giambalvo | 134/21 |
| 4,357,173 | 11/1982 | Rosenthal et al. | 134/6 |
| 4,444,307 | 4/1984 | Jermyn | 206/5.1 |
| 4,493,783 | 1/1985 | Su et al. | 252/174.23 |
| 4,533,399 | 8/1985 | Mencke | 134/6 |

(List continued on next page.)

FOREIGN PATENT DOCUMENTS

| | | |
|---|---|---|
| 2064438 | 10/1992 | Canada . |
| 1-287549 | 6/1991 | Japan . |
| 3-171032 | 7/1991 | Japan . |

OTHER PUBLICATIONS

"Cleaning Hydrophilic Contact Lenses: An Overview" by Stuart Eriksen, *Annals of Ophthalmology*, Sep. 1975, pp. 1223–1232.

"The Effect on Measured Visual Acuity of Protein Deposition and Removal in Soft Contact Lenses" by David A. McClure et al., *Contacto*, Mar. 1977, pp. 8–12.

"Deposits on Soft Contact Lenses. Electrophoresis and Scanning Electron Microscopic Examinations" by T. Bilbaut et al., *Exp. Eye Res*, 1968, pp. 153–165.

(List continued on next page.)

*Primary Examiner*—John Niebling
*Assistant Examiner*—John S. Starsiak, Jr.
*Attorney, Agent, or Firm*—Lockwood, Alex, FitzGibbons & Cummings

[57] ABSTRACT

A packet including substance and of a construction by which a lens may be encased and by which the application of treatment procedures to the lens is facilitated. The packet is useful in protecting the lens from possible damage during the period when the lens is separated from the cornea and is being treated. The packet is useful in a lens decontamination system that includes also a cleaning assembly in which the lens as encased within the packet is decontaminated. The packet includes surfaces positionable to contact the packet and through which electrical charges are transmitted to the lens. Under the influence of the electrical charges, contaminants are drawn off of and from below the surface of the lens.

6 Claims, 4 Drawing Sheets

U.S. PATENT DOCUMENTS

| | | | |
|---|---|---|---|
| 4,559,662 | 12/1985 | Kunold, Jr. | 15/104.94 |
| 4,582,076 | 4/1986 | Prat | 134/57 R |
| 4,607,652 | 8/1986 | Yung | 134/184 |
| 4,608,147 | 8/1986 | Clad | 204/301 |
| 4,609,493 | 9/1986 | Schafer | 252/546 |
| 4,613,379 | 9/1986 | Su et al. | 134/7 |
| 4,615,786 | 10/1986 | Culkin et al. | 204/301 |
| 4,619,747 | 10/1986 | Hoadley et al. | 204/182.8 |
| 4,631,120 | 12/1986 | Pohl | 204/182.8 |
| 4,668,359 | 5/1987 | Postle et al. | 204/182.7 |
| 4,732,185 | 3/1988 | Cowle et al. | 204/299 RX |
| 4,792,414 | 12/1988 | Su et al. | 252/174.12 |
| 4,839,082 | 6/1989 | Bhatia | 252/174.12 |
| 4,840,681 | 6/1989 | Pompe | 134/42 |
| 4,852,592 | 8/1989 | DiGangi et al. | 134/57 |
| 4,872,965 | 10/1989 | Pankow | 204/299 R |
| 4,998,590 | 12/1990 | Glorieux | 21/89 |
| 5,017,238 | 5/1992 | Chromecek | 134/7 |
| 5,037,484 | 8/1991 | Su et al. | 134/7 |
| 5,037,485 | 8/1991 | Chromecek et al. | 134/7 |
| 5,054,610 | 10/1991 | Ajello | 206/5.1 |
| 5,071,276 | 12/1991 | Nielsen et al. | 401/9 |
| 5,073,202 | 12/1991 | Wallach | 134/6 |
| 5,100,477 | 3/1992 | Chromecek et al. | 134/7 |
| 5,114,686 | 5/1992 | Gillespie | 422/300 |
| 5,127,126 | 7/1992 | Tanaka et al. | 15/214 |
| 5,128,058 | 7/1992 | Ishii et al. | 252/174.13 |
| 5,227,039 | 7/1993 | Pankow | 204/180.1 |

OTHER PUBLICATIONS

"Protein Migration Through Hydrogels: A Tool for Measuring Porosity—Application to Hydrogels Used as Contact Lenses" by A. M. Gachon et al. *Analytical Biochemistry*, (1968), pp. 249–255.

"Identification Prevention and Removal of Contact Lens Deposits", (booklet) *Optometry Documenta*, (1984).

LENS PROTECTIVE ENCASEMENT PACKET

This is a continuation-in-part of application Ser. No. 800,686 filed Dec. 12, 1992, now U.S. Pat. No. 5,227,034.

BACKGROUND OF THE INVENTION

The present invention generally relates to apparatus and methods by which contact lenses can be protectively encased. More particularly, the invention relates to apparatus including substance and of a construction by which a lens can be safely encased for the protection of the lens and by which the application of treatment procedures to the lens is facilitated. Advantageously, the present invention is useful in protecting the lens from possible damage during period when the lens is separated from the cornea and is being treated.

A contact lens is a small, shell-shaped device having a dominant concave surface and a dominant convex surface meeting at a dominant, curved surrounding edge. Contact lenses can be made of a variety of materials. Glass is one type of such material. However, in order to provide a lens that does not easily crack, that is light, in weight and that can conform to the varying contours of the cornea, lenses are now being made from materials other than glass. Plastic materials, such as hydrogel plastics, are one group of such materials from which lenses are now widely made. Hydrogel plastics have the unique property of being able to absorb and bind a proportionality large amount of water within a polymer network. A very flexible, pliant, and soft-feeling structure results. Lenses made from hydrated hydrogel plastics are comfortable to wear because they easily conform to the cornea of the eye.

However, one serious drawback associated with lenses, regardless of the material from which they are made, is that they are easily contaminated. The simple handling of the lens by the user, such as during the placement of or the adjustment of the lens on the eye, can deposit a variety of foreign organic and inorganic materials on the lens. Once in place on the eye, a lens readily collects the oily and sebaceous substances and protein secreted by the eye. A lens positioned on the eye can collect also airborne chemicals and biological agents such as bacteria, viruses, and fungus.

Contaminants generally remain at the surface of the lenses made from the harder, non-porous materials, such as glass. However, lenses made from hydrogel plastic materials, when hydrated, form a porous polymer subsurface network into which water-soluble substances and ions can readily enter and become lodged. With time, and especially after one or more attempts to clean the lens through known cleaning techniques, the surface of the hydrogel lens tends to develop pin holes, cracks, and/or microscopic defects. Into and through these openings, proteins and pathogens, such as viruses and bacteria, can move. Through this mechanism, contaminants can collect not only at, but also below the surface of the lenses made from the new softer materials.

The contamination of lenses is a variable, but generally rapid occurring phenomenon. It has been found that fifty percent of a lens surface may be covered by deposits after a lens has been worn for only thirty minutes. After 8 hours, ninety percent of the lens surface may be coated. Complete coverage occurs typically within a matter of weeks.

Contaminants can degrade the optical performance of a lens. Sufficient layers of contaminants can accumulate on and within the lens to form a colored and/or partially opaque layer of oil, mucous, and crystalline deposits. The amount of light transmitted through the lens—and, therefore, visual acuity—diminishes depending on the composition, thickness, and extent of the contamination coating.

Contaminants can degrade also the mechanical performance of a lens by roughening the surface of a lens. The once smooth, easy-to-wear device, across whose convex surface the wearer's eyelid can glide, is transformed with time into a roughened source of irritation. Abrasions and giant papillary conjunctivitis may follow.

The cornea of the eye remains healthy and transparent only if it is kept wet and oxygenated. The tear film normally keeps the corneal epithelium wet and supplies it with oxygen from the atmosphere. The tears that can flow under and around a clean lens normally keep the cornea wet and oxygenated. However, contamination of a lens can ultimately decrease the amount of tears, and thereby the oxygen delivered to a lens. When the cornea is deprived of oxygen, anaerobic glycolysis is caused. The cornea can swell and become hazy.

A coating of contaminants on a lens can physiologically affect the eye in other ways. Contaminants can serve as an environment in which microorganisms, such as bacteria, fungi, and yeast, can flourish. Conditions such as conjunctivitis may result.

A variety of agents and techniques have been devised in an effort to remove contaminants from a lens. Known agents—such as surfactants, oxidants, disinfectants, enzymatic cleaners, and abrasives—and techniques, such as those utilizing the described agents and others, are typically directed to the removal of only one or a few types of contaminants that may collect on the surface of a lens.

Other conventional agents, methods, and devices are not necessarily directed to the removal of contaminants from the lens but to the deactivation of the pathogenic component of the contamination layer. One example of such a bacterial deactivation device is taught in U.S. Pat. No. 4,202,740.

In an attempt to improve the effectiveness of some of these known agents and techniques, mechanical devices are often used in combination with them. Such mechanical devices vibrate, rotate, scrub, heat, agitate and/or direct ultrasonic waves to a lens in an attempt to further dislodge and/or deactivate those elements fouling a lens.

Conventional cleaning agents and methods, even with the assistance of conventional mechanical devices, are limited in their effectiveness. Some of these agents, methods, and devices may be able to remove a portion of the contaminants from the surface of a lens, yet are largely unable to remove the large percentage of contaminants from and below the surface of lenses made from the newer, softer materials.

In addition to having limited effectiveness in the removal of contaminants, some techniques and devices can actually exacerbate the contamination problem by denaturing the protein component of the contamination coating. An intractable layer of contamination forms. With time, and as new layers of contaminants accrete on the older layers of contaminants, the contamination layer extends and thickens. Because of the increased irritation and the decreased visual acuity caused by this layer, lenses must eventually be replaced with new lenses. Typically, the replacement of lenses is required within one year.

Other conventional lens cleaning and/or contamination removal agents, methods, and devices may cause damage to lenses particularly those made from the newer, softer materials. For example, abrasive powders, pads, and solutions are known to remove some of the contamination from the surface of the lens. However, the use of such abrasives can scratch or otherwise damage the surface of the lens.

Other agents, methods, and devices may produce byproducts that can cause damage to a lens. For example, certain conventional devices and techniques immerse contact lenses in a fluid bath through which an electric current is established. However, these devices are constructed and/or may be used such that the electric current is of a sufficiently high voltage that dissociation of the elements of the fluid bath is caused. Depending on the composition of the fluid bath, chemical species such as $Cl^-$ or $HClO$ may be produced. While these chemical species may kill, for example, bacteria on the lens immersed in the electrified bath, they also may also damage the material from which the lens is made.

In response to the demand for apparatus and methods by which a wide range of contaminants can be removed efficiently and safely from contact lenses, the inventor of that which is described in the present application has invented a novel lens decontamination system. The system removes contaminants from and below the surface of a lens electrokinetically by the complete application of opposing electrical charges to the lens and without the need for the total immersion of the lens in a fluid bath. The lens decontamination system is the subject of an application for Letters Patent filed concurrently with and incorporated completely by reference in this application.

The present invention is directed to the protection of a lens during the period it is separated from the eye and by which the treatment of lens can be facilitated, such as through the use of the lens decontamination system taught in the copending patent application.

The present invention is a packet. The packet is of a structure and includes a substance or substances by which a lens can be protectively encased and which facilitates the treatment of the lens. Such treatment includes the cleaning of the lens, such as that directed to the deactivation of pathogens and organisms on the lens and that directed to the removal of contaminants from the lens. One embodiment of the present invention, for example, facilitates the complete application of electrical charges to the entire surface, including the edge area of a lens, such as with the system taught in the copending patent application. Such treatment includes also surrounding a lens in a moist environment to maintain a lens at its optimum moisture level.

The substance or substances may be sufficiently pliant so that the entire surface of the lens, including the surrounding edge area, can be covered thereby. The entire surface of a lens stored within the packet, accordingly, can be treated.

The packet substance or substances may be composed of material that can accept and retain moisture. The packet substance or substances may also have an appreciable moisture content. Advantageously, a hydrated lens encased within such moist substance or substances does not dry out after separation from the cornea.

Compared to the more complex, multi-component conventional lens storage containers, the packet of the present invention is of a simple construction. One embodiment of the packet includes separate sections that open to provide opposing faces between which a lens can be completely encased and without the damaging bending, compression, and/or contortion of the lens.

The packet preferably ensures that pathogens and/or contaminants on or within a lens that is being treated cannot readily migrate to the outside of the packet. Such a packet provides a closed encasement system that allows a lens to be treated without the danger of contamination or infection of other individuals or surfaces.

While the packet may be made from material that can be reused, the packet may be made also from materials that are generally intended for a single treatment procedure and disposal. Any health risks associated with the treatment of a contaminated contact lens are thereby lessened.

The packet preferably includes also simplified opening and closing means, thereby facilitating the use of the packet by even those with temporarily limited vision.

As a means for storing a lens, the present invention has a variety of advantages over conventional devices. Conventional storage devices, such as those in which lenses are stored during a cleaning procedure, generally consist of containers having multiple pieces, including doors, covers, or lids that must be fitted, snapped, or screwed together, or closed in order to form a storage space. It is not uncommon for an individual—particularly one who has removed his or her lenses and, accordingly, has limited vision—to knick or catch a portion of the lens during the fitting, snapping, screwing, or closing of the doors, covers, or lids of the container. Furthermore, the storage space provided by known containers is such that a lens is generally only loosely held during a treatment procedure. Accordingly, the likelihood that a lens will be contorted, bent, overly compressed, or otherwise damaged while held within one of these devices and subjected to known treatment techniques, such as spinning, vibrating, or heating, and/or ultrasonic treatment, is increased.

Certain preferred embodiments of the present invention are structured and including substance or substances such that a lens can be treated according to the lens decontamination system taught in the copending application. This system includes a cleaning assembly. The packets embodiments useable in this system include a substance or substances and a structure by which opposing electrical charges can be transferred to the entire surface, including the surrounding edge of the lens. In order to treat a lens according to this system, the user places his or her lens in the protective encasement packet. The packet is placed in the cleaning assembly such that the outer faces of the packet contact electrically chargeable surfaces exposed from the assembly. In such a position, opposing electrical charges are transferred from the charged assembly surfaces through the packet substance or substances and to the lens. Contaminants are drawn from the lens and into the substance or substances. After the application of electrical charges, the packet is removed. The lens is removed from the packet. After, for example, rinsing and soaking in saline solution, the lens may be placed back onto the eye. Accordingly, the lens, including lens edge area, as completely encased during the treatment procedure, is entirely cleaned and in less time than conventional methods. The partial cleaning or shadow effects of conventional apparatus and methods that enclose or partially enclose a lens within a container is avoided. The preferred embodiments of the present invention also eliminate the need for the coordinated and time-consuming use of, for example, a container for holding fluids, fluids, and tablets that some conventional treatment procedures require. To prevent contamination and/or infection of other surfaces or individuals and in order to facilitate clean-up, the packet may be made of inexpensive materials allowing the packet to be discarded.

It is, accordingly, a general object of the present invention to provide apparatus and methods by which a lens can be completely protected during the period it is separated from the cornea.

Another object of the present invention is to provide apparatus by which a lens, including its dominant curved surfaces and surrounding edge, can be completely encased and without damage to the lens.

Also an object of the present invention is to provide apparatus including a substance or substances by which a lens can be protectively encased and that facilitates the treatment of the lens.

A further object of the present invention is to provide apparatus including a substance or substances in which a lens can be protectively encased and by which treatment may be applied to opposing sides and the edges of a lens.

An added object of the present invention is to provide apparatus including a substance or substances in which a lens can be protectively encased and that facilitates the uniform treatment of a lens by the complete application of electrical charges to the entire surface of a lens.

An additional object of the present invention is to provide apparatus including a substance or substances through which electrical charges may be transferred uniformly to the entire surface of a lens and into which contaminants are removed from the lens.

Another object of the present invention is to provide a closed system for the protective encasement and treatment of a lens.

An added object of the present invention is to provide apparatus including a substance or substances into which contaminants removed from a lens are trapped to prevent contamination and infection of other surfaces or individuals.

These and other objects, features, and advantages of the invention will be clearly understood and explained with reference to the accompanying drawings and through a consideration of the following detailed description of the preferred embodiments.

DESCRIPTION OF THE PREFERRED EMBODIMENTS

Figure 1:
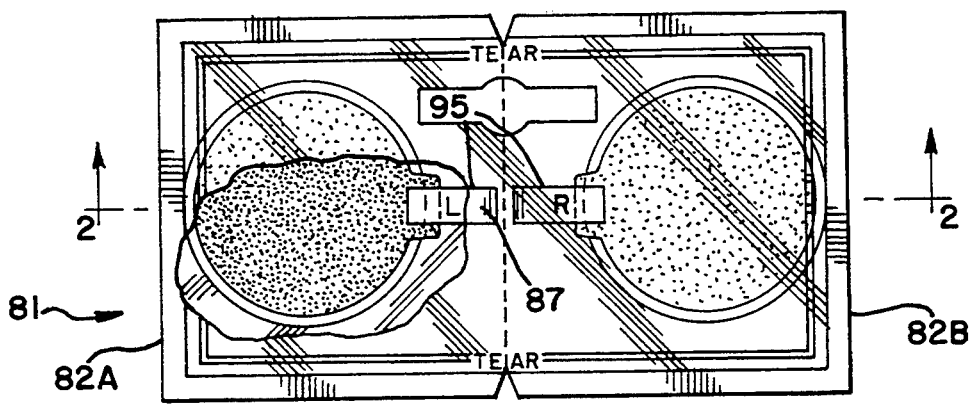
FIG. 1 is an overhead, partially cut-away view of a pair of one embodiment of protective encasement packets according to the present invention as contained within one embodiment of a package.
Figure 2:
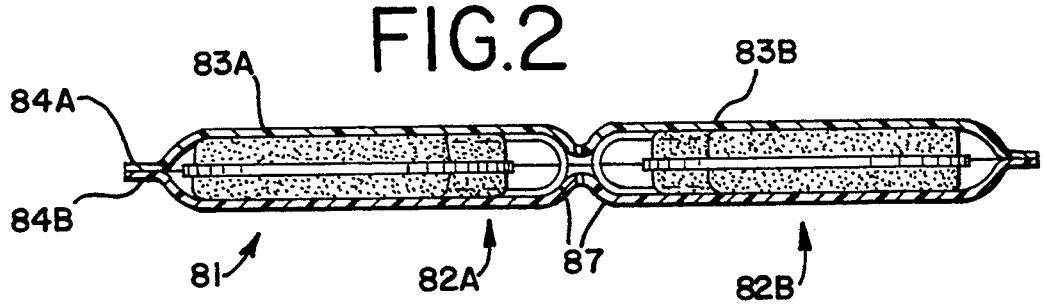
FIG. 2 is a sectional view through the pair of encasement packets as contained within the package illustrated in FIG. 1.
Figure 3:
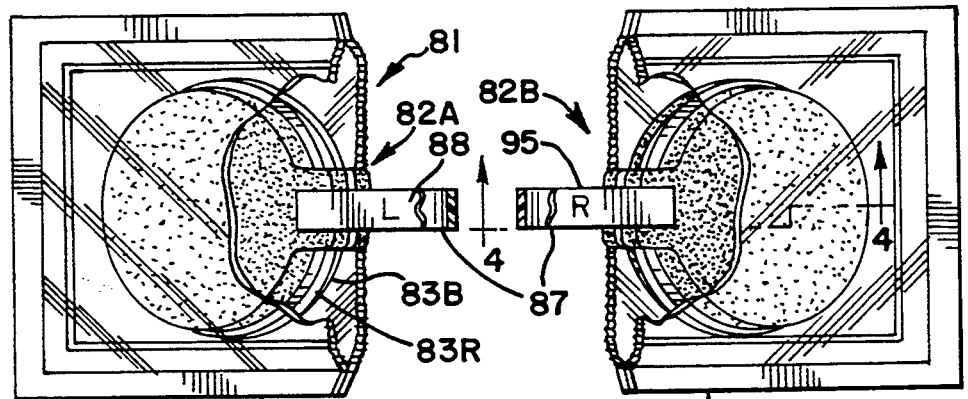
FIG. 3 is a partially sectional view through the packet embodiment and package embodiment illustrated in FIG. 1 and FIG. 2 showing a pair of protective encasement packets conveniently exposed for removal upon the opening of the package.
Figure 4:
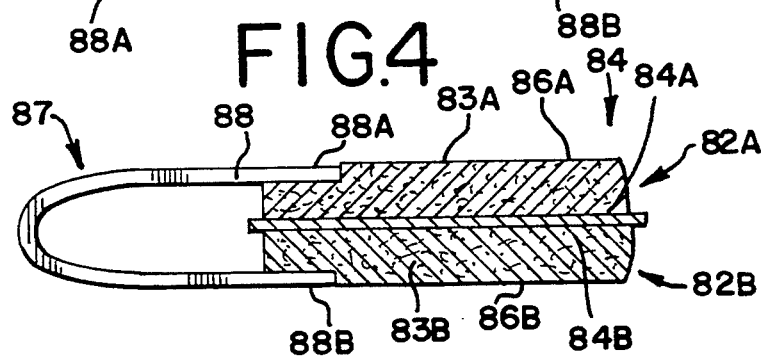
FIG. 4 is a sectional view of one of protective encasement packets illustrated in FIG. 3.

A protective encasement packet according to the present invention is designated in FIGS. 1 through 17 as 81.

Packet 81 includes a substance or substances by which a lens 101 can not only be completely covered, and thereby protectively encased, such as after the lens has been removed from the eye, but also that facilitates the treatment of the lens. Substances by which a lens can be completely covered include pliable materials. Suitable pliable materials include formaminous materials, such as foam or natural or artificial sponge and microporous materials. Other suitable pliable materials include paper—such as ashless paper typically used in the laboratory. Such materials advantageously provide an open porous structure having a large internal and external surface area. Such materials accept and retain moisture applied to the material thereby maintaining a lens enclosed within the materials in a hydrated state. Materials having such a porous structure also accept and generally retain contaminants that are pulled from the lens during the cleaning process.

Because suitable materials may have a low moisture content, a moistening agent may need to be added to such materials, particularly to facilitate the treatment of the lens without the appreciable loss of moisture from the lens, and in order to facilitate the treatment of the lens according to the decontamination system taught in the copending patent application. The composition of the moistening agent can be varied according to the type of treatment to be applied to the lens.

For example, the moistening agent for material in a packet used simply to maintain or to attain the optimum hydration level of the lens and not necessarily for purposes of subjecting the lens to a treatment procedure in which the dissociation of chemical species may occur, may be water or water with an additive or additives, such as salt.

The moistening agent for material used in a packet in which a lens is encased and is treated according to the system taught in the copending application is preferably free of sodium or chlorine to prevent the possible production of chemical species harmful to the lens. Such harmful species are $Cl^-$ or $HClO$.

Depending on the treatment procedure and to prevent the formation of chemical species, such as radicals that may cause damage to the lens, the moistening agent may include also a buffer. Preferably, the buffers should be free of an ionizable halide ion—such as $Cl^-$, $Fl^-$, or $Br^-$—and an ionizable reactive metal ion—such as sodium or calcium. Suitable buffers include those that are known by the following acrynonyms: ACES, BES, BICINE, BIS-TRIS, DIPSO, EPPS or HEPPS, MES, MOPS, PIPES, POPSO TAPS TAPSO and TES. Depending on the treatment procedure, amino acids, polyamine acids, or polybuffers may also be used as buffers.

The moistening agent may include also a detergent. A detergent is useful to loosen and/or remove altogether lipids and other insoluble materials. Whether a charged or non-charged detergent is used, and if a charged detergent is used, whether an anionic, cationic, or zwitterionic detergent is used, depends largely on the type of contaminant that the user wishes to remove from the lens. Suitable anionic (that is, negatively charged) detergents, include caprylic acid, choleic acid, 1-decase sulfonic acid, deoxycholicacid, and lauryl sulfate. Suitable cationic (that is, positively charged) detergents include catylpyriclinium chloride and do-, Hexa-, or tetradecyl-trimethylammonium bromide. Suitable zwitterionic detergents include CHAPS, N-Octadecyl-N, N - dimetryl 3-ammonio-1-propamesulfonate, and phosphatidyl, choline, dipalmitoy.

The material may be pre-moistened to provide a packet suitable to accomplish one or more treatment procedures. The moistening agent also may be separately provided to allow a user to prepare the material just prior to the desired treatment procedure.

The packet may be formed from or include also materials that are particularly suited to facilitate the transfer of electrical charges externally applied to the packet but do not require moistening. Known charge conducting artificial composite materials and conductive metal foils are representative of such materials.

The packet may be formed from or include also materials that slow and/or block the further migration of contaminants pulled from the lens. These materials include known filter or membrane materials such as charged or uncharged nylon or cellulosic polymers having an average pore size that is below the generally expected size of the contaminants pulled from the lens.

Other substances—having an appreciable water content and that are suitable to protectively enclose and facilitate the treatment of a lens—may be used with the above described materials or alone. Such substance include hydrated protein, such as agar and jelly, and the materials including microcrystalline cellulose and fumed silica. These substances are generally very pliant and, accordingly, easily conform to the surfaces and edge of the lens. Additionally, these substances have a sufficient moisture content to lessen or altogether prevent any dehydration of the lens. The moistening agent may include the buffering agent. Because of the high moisture content of these substances, electrical charges are easily transmitted through these substances.

Protective encasement packet 81 is further of a structure to facilitate the protective encasement and complete treatment of the lens. Those packets that include components in addition to the above described preferred substance or substances preferably are structured so that a lens may generally contact only a soft pliant substance or substances while being inserted or removed from the packet. Such a structure lessens or eliminates the likelihood that the lens will be scratched or otherwise damaged. For example, FIGS. 1 through 17 illustrate embodiments of a packet 81 separated into sections 82. The pliant material of each of the packets 81 illustrated in FIGS. 1 through 17 includes sections 82A, 82B. Each section 82A, 82B includes a pad 83A, 83B. Each of these pads 83A, 83B includes a face 84A, 84B composed of pliant material that will be generally contacted as the lens is placed within the packet 81 and by which the dominant curved surface and edge area of the lens 101 can be completely covered. Packet 81 may include opposing faces 84A, 84B that when joined over a lens completely cover the dominant surfaces of the lens and touch at and overlap beyond the surrounding edge of the lens. So that packet 81 can be used to protectively encase and treat lenses of a variety of diameters, one or both faces 84A, 84B may be of a size larger than the diameter of the largest contact lens generally available.

The construction of the packet and the range of suitable substances will become further apparent from the following more specific discussions of the illustrated preferred embodiments.

Each section 82A, 82B of the packet embodiments illustrated in FIGS. 1 through 17 includes a pad 83A, 83B having opposing inner faces 84A, 84B composed of a surface and substance by which a lens 101 can be completely covered without causing damage to the lens. The sections 82A, 82B are joinable to completely encase the lens and such that the substance meets at the edge area of the lens, thereby ensuring complete treatment of the lens surface and edge.

Figure 5:
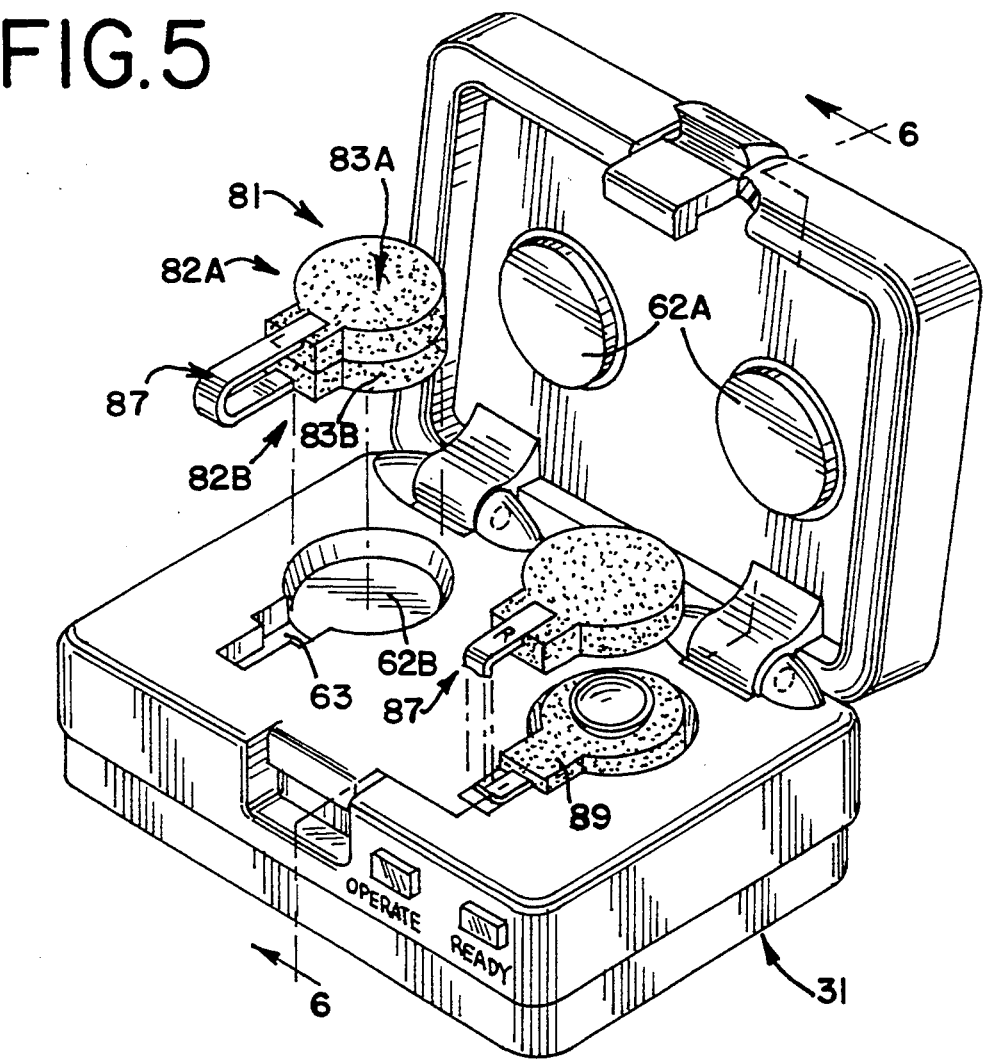
FIG. 5 illustrates the lens decontamination assembly taught in the copending patent application showing the use of the embodiment of the protective encasement packets illustrated in FIGS. 1 through 4 to protectively encase lenses during a treatment procedure.
Figure 6:
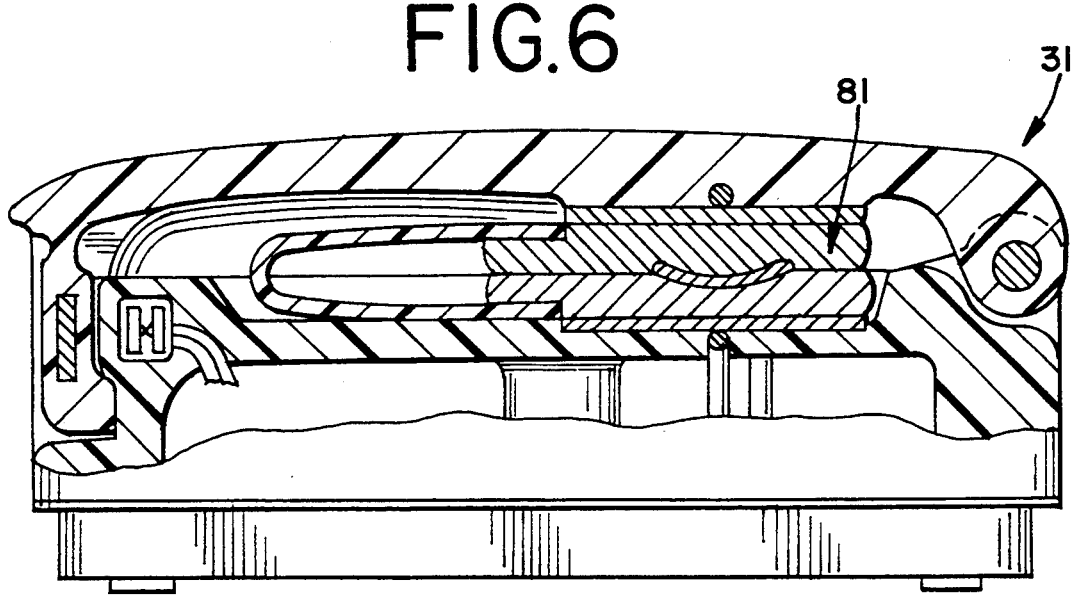
FIG. 6 is a sectional view of the protective encasement packet as fitted onto surfaces of the assembly illustrated in FIG. 5.
Figure 7:
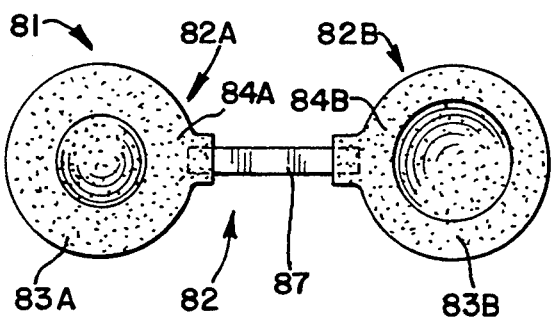
FIG. 7 is an overhead view of another embodiment of a protective encasement packet in an open position and showing faces of the packet having curved faces that approximate the curved surfaces of a lens.
Figure 8:
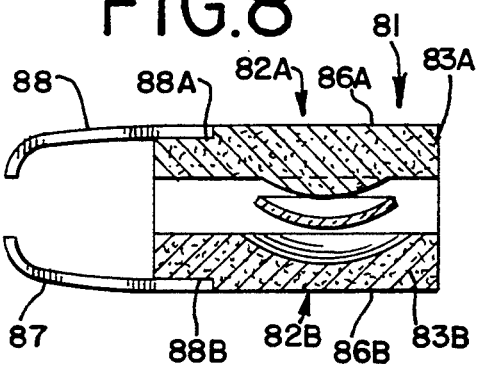
FIG. 8 is a sectional view of the embodiment of the protective encasement packet illustrated in FIG. 7 and showing a lens positioned between the curved faces of the packet.
Figure 9:
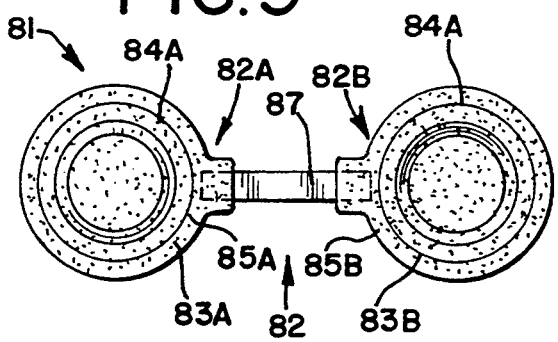
FIG. 9 illustrates another embodiment of the protective encasement packet in an open position and showing a convenience structure that facilitates the positioning of a lens between the faces of the packet.
Figure 10:
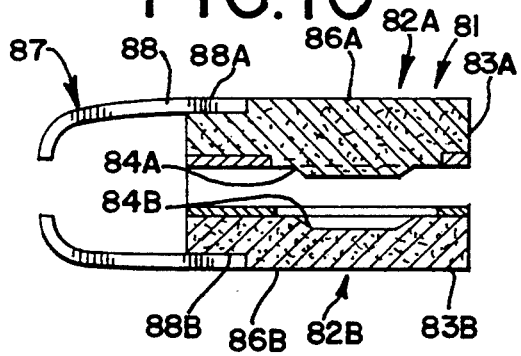
FIG. 10 is a sectional view of the embodiment of the protective encasement packet illustrated in FIG. 9 and showing the alignment of the packet sections for the reception of a lens therebetween.
Figure 11:
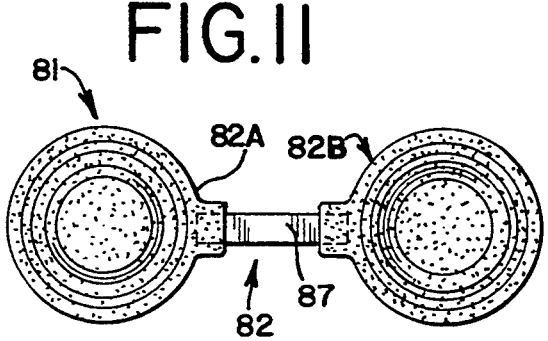
FIG. 11 illustrates another embodiment of the protective encasement packet in an open position and showing an overhead view of the packet faces including securement elements.
Figure 12:
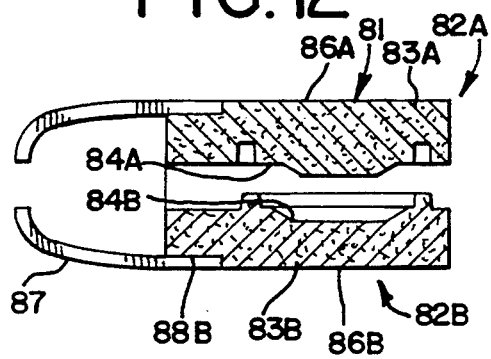
FIG. 12 is a sectional view of the embodiment of the protective encasement packet illustrated in FIG. 11 and showing the groove-shaped profile and the rib-shaped profile securement elements.
Figure 13:
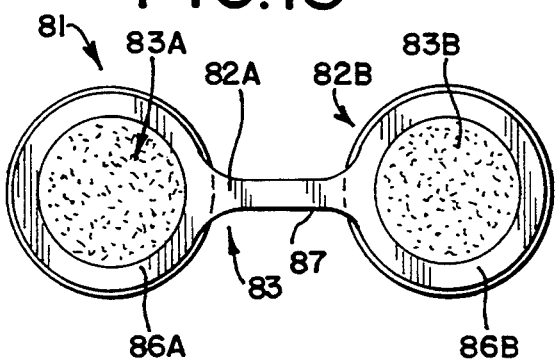
FIG. 13 illustrates another embodiment of the protective encasement packet in an open position and showing an overhead view of the packet's outer faces and an embodiment of the tab that is continuous around the edges of the outer faces of the packet.
Figure 14:
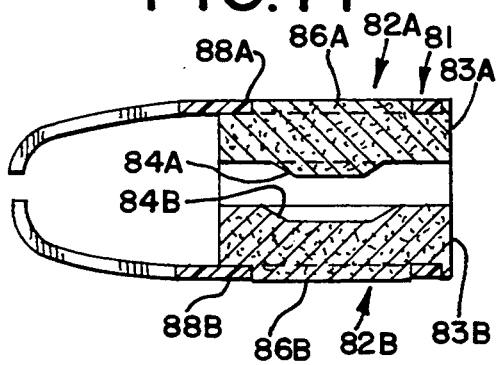
FIG. 14 is a sectional view of the embodiment of the protective encasement packet illustrated in FIG. 13.
Figure 15:
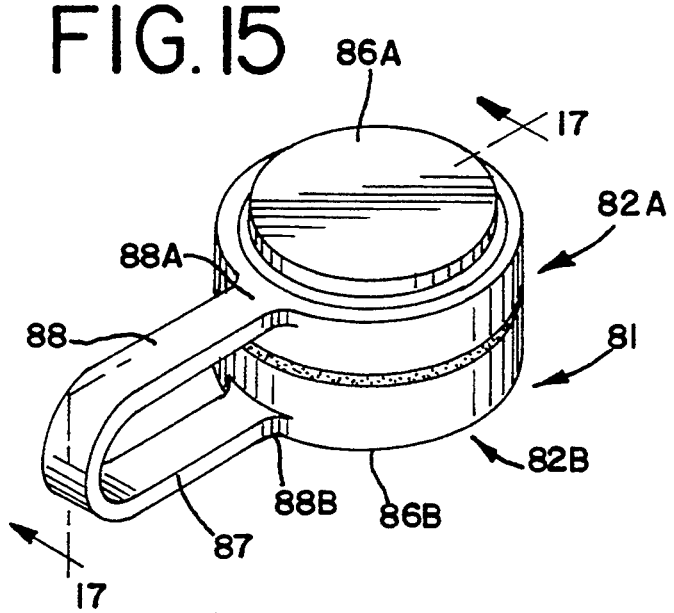
FIG. 15 is a perspective view of another embodiment of the protective encasement packet and showing an embodiment of the tab that is continuous around the outer edges of the packet pad and including a contact element.
Figure 16:
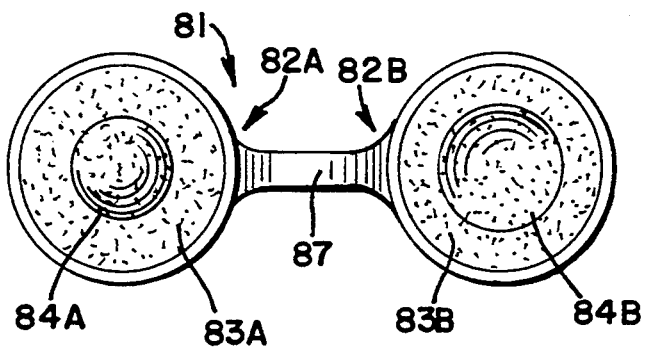
FIG. 16 is an overhead view of the protective encasement packet illustrated in FIG. 15 and showing the inner faces shaped to receive a lens therebetween.
Figure 17:
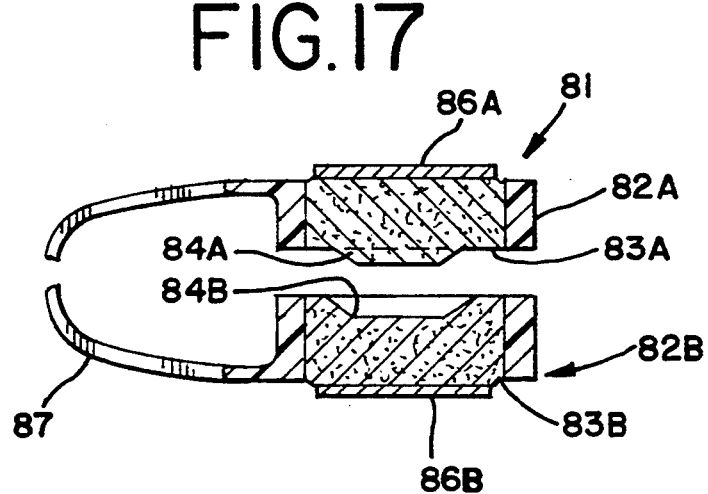
FIG. 17 is a sectional view of the protective encasement packet illustrated in FIG. 15.

FIGS. 1 through 6 illustrate an embodiment of the packet 81 having sections 82A, 82B including pads 83A, 83B composed of pliant foam. FIGS. 5 and 6 illustrate this embodiment of the packet 81 used in conjunction with the decontamination system to which the copending patent application described above is directed. According to this system, a lens is treated by the application of electrical charges to the dominant surfaces and edge of the lens. It is preferred that low voltage and amperage charges be used to decontaminate the lens. To decontaminate a lens with a low voltage and amperage, the distance between the charge transmitting surfaces of the decontamination apparatus and the lens surface are preferably kept to a minimum. In order to do so, the substance or substances used to protectively encase the lens is used only in that thickness such that the lens surface is completely covered but without added thickness. FIG. 5 illustrates the use of two packets 81 with a lens 101 encased between the faces 84A, 84B of each packet 81.

Packets 81 may include material that slows the passage of contaminants or does not allow, for example, contaminants to migrate outside the packet but allows the lens encased therein to be treated. Such material may provide an outer surface covering to a substance that is generally pliant, such as the illustrated foam. Alternatively, the packet 81 may be formed entirely of the same material.

The packet 81 may include material such as a metal foil by which the treatment of lenses by electrical charges, such as that described in the copending patent application, may be facilitated.

Packets 81 may include positioning means 85 to facilitate the reception of the lens thereon. Such positioning means 85 includes a generally pliant ring placed on the inner face of the pad 83. The embodiment of the packet 81 illustrated in FIGS. 9 and 10 includes separate rings 85A, 85B positioned adjacent to and encircling the faces 84A, 84B of the packet.

Because of the preferred generally pliant nature of the substance or substances from which the packet 81 is made, other elements 85 may be added to define the scope of, support, and/or aid in the alignment of these materials. For example, the embodiments of the protective encasement packet 81 illustrated in FIGS. 1 and 17 each include a tab 87. The tab 87 is of a material or materials and structured so that the face of one section, such as face 84A, can be movably aligned opposite to the face 84B of the other section, such as face 84B. While tab 87 may have a variety of constructions and be composed of a variety of materials to facilitate the movable alignment of the sections 83, the embodiment of the tab 87 illustrated in FIGS. 1 and 17 includes a band 88 having ends 88A, 88B connected to sections 82A, 82B. The illustrated tab 87 may be composed of generally pliant material, such as a plastic, so that the tab 87 can be subjected to bending without cracking.

Each packet 81 may contain means 95 by which a user can distinguish into which packet 81 the user placed his or her left lens and/or the right lens. The maintenance of the identity of each lens is generally necessary because of the varying corrective prescriptions each lens may have. These identification means may include separate colors, words, symbols. For example, the embodiment of the packet 81 shown in FIGS. 1 and 3, include an "L" visible on the tab 87 of one packet 81 for the packet left eye lens and a "R" visible on the tab 85 for the packet 81 in which a user may place his or her right eye lens.

Each packet 81 may further include features which cooperates with a treatment apparatus to further allow the packet to retain a desired alignment throughout a treatment procedure. For example, the FIG. 5 embodiment of the packet 81 includes an alignment component 89. The alignment component 89 of the illustrated packet 81 is formed from uniform extensions of each packet section 82A, 82B. The alignment component is sized and shaped to be received within accommodation space 63 that opens from each transmitting surface 62. The illustrated accommodation space 63 is sized and shaped to further receive a tab 87 of each packet 81. Accordingly, after a lens 101 is placed in the packet 81, the packet 81 is positioned in contact with the charge transmitting surfaces 62A, 62B and such that the tab 87 and alignment component 88 are received within the accommodation space 63.

A lens 101 may be treated with the use of the present invention according to the following methods. In those embodiments of the packet 81 in which one or more substance or substances is moistened to facilitate the transmission of an electrical charge, the substance or substances is moistened. Each lens 101 that is to be treated is placed in a packet 81. In the embodiment of the packet 81 illustrated in FIGS. 7 through 17, each lens is placed such that the dominant convex surface of the lens and is placed completely in alignment with the concave face 84B of a section 82B. The other section 82A of the packet 81 having a convex shaped face 84A is aligned to completely cover the dominant concave face of the lens. The charge transmitting areas 61 are positioned such that the charge transmitting surfaces 62A, 62B of each area 61 contact the outer faces 86A, 86B of the packet 81 within which the lens 101 is encased. According to the embodiment of the lens decontamination system illustrated in FIGS. 5 and 6, the outer face 86B of one section 82B of the packet 81 is placed on the surface 62. Each tab 87 and alignment component 89 is placed in the accommodation space 63. Cover 34B is drawn over the packet 81 such that the outer face 86A of the other section 82A of the packet 81 is contacted by surface 62A. When the treatment of the lens 101 consists of decontamination according to the system to which the copending patent application is directed, the electrical charges are transmitted from the surfaces 62, to the outer faces 86A, 86B of the packet 81, to the substance or substances below the faces 86, and onto the surfaces of the lens. Because the inner face 84A, 84B of each section 83 completely surrounds and extends beyond the edge of the lens 101, the face 84A, 84B of each section 83A, 83B contacts each other. This overlap ensures that the surrounding edge of the lens 101 is treated in addition to the dominant curved surfaces of the lens. In a lens treated by the application of electrical charges an electrical current is generally established through the lens and not around the lens. This is due to the fact that the current seeks the path of least resistance which is generally through the lens since it has a generally higher water content than the surrounding substances.

Contaminants absorbed on or trapped within the body of the lens migrate off of and from within the lens under the influence of the charges. Generally within minutes, the lens 101 may be largely decontaminated. With the use of a timer within the system and/or simply by opening the cover of the illustrated embodiment of the assembly 31, the application of electrical charges to the lens or lenses may be ceased. The packet 81 with lens 101 encased therein is removed from the assembly. The lens is removed from the packet. Depending on the substance included within the packet 81, the packet may be discarded with contaminants trapped therein or may be cleaned for reuse. Any contaminants dislodged and remaining on the surface of the lens may be rinsed away, such as with a solution containing a detergent and rinsed with water. The lens is then suitable for placement back onto the cornea.

While a particular embodiment of the invention has been shown and described, it will be obvious to those skilled in the art that changes and modifications may be made therein without departing from the invention in its broader aspects, and, therefore, the aim in the appended claims is to cover all such changes and modifications as fall within the true spirit and scope of the invention.

I claim:

1. A protective encasement packet for removing contaminants from a contact lens by the application of electrical charges, said lens having curved dominant surfaces and a surrounding edge at which said dominant surfaces generally meet, said packet comprising:

a pliant porous substance through which the electrical charges can be transmitted, said substance being formable to provide inner faces, said inner faces sized and shaped to cover said dominant surfaces and said surrounding edge of said lens, said pliant porous substance further including outer faces sized and shaped to accept the electrical charges and transmit the charges to said inner faces and thereby to said lens, whereby said lens as covered can be treated by such charges; and a blocking layer comprised of an electrically conductive membrane material overlying each of said outer faces for preventing the migration of said contaminants outside of said outer faces.

2. Apparatus for removing contaminants from a contact lens by the application of electrical charge, said lens having a dominant convex surface, a dominant concave surface, and a surrounding edge, said apparatus comprising:

a pair of outer membrane members each forced of electrically conductive material impervious to said contaminants, said membrane members each including an outer surface sized and shaped to accept the electrical charge and an inner surface;

a pliant porous substance positioned on said inner surfaces and through which the electrical charge is transmissible from said membrane members to the lens, said substance being formable to provide an inner face on which said lens can be aligned and completely covered;

whereby said lens as aligned and completely covered by said inner face is treatable by the application of the electrical charge to and through said membrane members and thereby to and through said positioned substance and to said aligned and covered lens.

3. The treatment apparatus according to claim 2, wherein said membrane members each comprise a metal foil layer across which electrical charge can be transmitted and by which contaminants are prevented from crossing to said outer surface of said apparatus.

4. The treatment apparatus according to claim 2, wherein said substance is gelatinous.

5. The treatment apparatus according to claim 2, wherein said substance includes a buffered moistening agent.

6. Method for removing contaminants from a contact lens with the application of electrical charges, said lens having a dominant convex surface, a dominant concave surface, and a surrounding edge, said method comprising:

positioning a lens on inner faces of a treatment packet including a formable pliant substance by which a lens can be treated, and a pair of outer membrane layers formed of electrically conductive material impervious to the contaminants;

closing said packet such that said dominant convex surface, said dominant concave surface, and said surrounding edge of said lens are completely covered by said substance;

aligning said outer membrane members with respective ones of said dominant lens surfaces on the outer surface of said substance; and charging said outer membranes members such that an electric current is caused to pass through the lens whereby said lens is decontaminated.

* * * * *